(12) United States Patent
Hayashizaki (10) Patent No.: US 7,122,382 B1
(45) Date of Patent: Oct. 17, 2006

(54) METHOD FOR DETECTING PROTEINS UNDER MUTUAL INTERACTION

(75) Inventor: Yoshihide Hayashizaki, Tsukuba (JP)

(73) Assignee: Riken, Wako (JP)

( * ) Notice: Subject to any disclaimer, the term of this patent is extended or adjusted under 35 U.S.C. 154(b) by 0 days.

(21) Appl. No.: 09/959,768

(22) PCT Filed: Apr. 28, 2000

(86) PCT No.: PCT/JP00/02802

§ 371 (c)(1),
(2), (4) Date: Feb. 4, 2002

(87) PCT Pub. No.: WO00/68690

PCT Pub. Date: Nov. 16, 2000

(30) Foreign Application Priority Data

May 7, 1999 (JP) .................................. 11-127586
Aug. 6, 1999 (JP) .................................. 11-224269

(51) Int. Cl.
*G01N 33/543* (2006.01)
*G01N 33/53* (2006.01)

(52) U.S. Cl. .................... 436/518; 435/7.1; 435/7.5; 435/7.92; 436/501; 436/524; 436/824

(58) Field of Classification Search ............... 435/6, 435/7.1, 7.5, 7.92, 971; 436/501, 518, 524, 436/536, 824
See application file for complete search history.

(56) References Cited

U.S. PATENT DOCUMENTS

| 5,635,182 A | * | 6/1997 | McCoy et al. ........... 424/192.1 |
| 5,639,597 A | | 6/1997 | Lauffer et al. |
| 5,643,722 A | * | 7/1997 | Rothschild et al. ............. 435/6 |
| 6,156,511 A | * | 12/2000 | Schatz et al. ................... 435/6 |
| 6,197,599 B1 | * | 3/2001 | Chin et al. ................... 436/518 |
| 6,329,209 B1 | * | 12/2001 | Wagner et al. .............. 436/518 |
| 2001/0039011 A1 | * | 11/2001 | Yanagawa et al. ............. 435/6 |
| 2002/0076799 A1 | * | 6/2002 | Wang ......................... 435/226 |

FOREIGN PATENT DOCUMENTS

| EP | 0 770 876 B1 | | 4/2001 |
| GB | 0234799 | * | 9/1987 |
| JP | 06-225783 | | 8/1994 |
| JP | A6-225783 | | 8/1994 |
| JP | 9-178746 | | 7/1997 |
| JP | 9-507760 | | 8/1997 |
| JP | 10-295375 | | 11/1998 |
| JP | A10-295375 | | 11/1998 |
| WO | 96/14426 | | 5/1996 |
| WO | WO 97/45745 A1 | | 12/1997 |

* cited by examiner

*Primary Examiner*—Long V. Le
*Assistant Examiner*—Gary W. Counts
(74) *Attorney, Agent, or Firm*—Birch, Stewart, Kolasch & Birch, LLP (57) ABSTRACT

A method for detecting proteins under mutual interaction which comprises mixing a protein having a label for detection synthesized by a cell-free protein synthesis method with another protein having a modification for separation, or synthesizing a protein having a label for detection and another protein having a modification for separation in a single system by the cell-free protein synthesis method; separating a pair of proteins formed by the interaction between these proteins with the use of the modification for separation as described above; and distinguishing these proteins with the use of the label for detection as described above. A screening method using this method.

14 Claims, 2 Drawing Sheets

METHOD FOR DETECTING PROTEINS UNDER MUTUAL INTERACTION

This application is the national phase under 35 U.S.C. § 371 of PCT International Application No. PCT/JP00/02802 which has an International filing date of Apr. 28, 2000, which designated the United States of America.

TECHNICAL FIELD

The present invention relates to methods of detecting proteins interacting with a given protein, and methods employing this method to detect those proteins in a group of multiple proteins that are capable of interacting with any of the proteins in another group of multiple proteins. Still further, the present invention relates to a method of screening protein pairs where a substance—a given compound, for example—affects interaction between proteins.

BACKGROUND OF INVENTION

It is common knowledge that certain proteins interact with certain other proteins. The interaction between proteins is closely associated with the expression of certain physiological activity and serves as an indicator of the type of physiological activity of a given protein. Thus, when a new protein is discovered, the types of protein with which the new protein interacts provide a substantial hint as to the physiological activity of the protein.

Current well-known methods of analyzing interactions between proteins include immunoprecipitation, the phage display method, and the yeast two-hybrid system. In immunoprecipitation, an antibody (anti-A) against a given protein A is prepared and the protein B that coprecipitates with antigen A when anti-A is applied is specified; this method has been widely employed for some time. In the phage display method (for example, Clackson, T., and Wells, J. A., Trends Biotechnol., 12 (1994) 173–184), the phage library, in which various foreign gene fragments are inserted into the coat protein gene of a phage, and expressed as the fused protein with the coat protein, is employed. If a phage expressing protein B is detected using a protein A, the gene for protein B can be specified. In this method, the gene of A can also be specified if the antibody is employed as protein A. Further, when a gene library incorporating random mutations is employed, it is possible to isolate and identify the genes of mutant proteins capable of acting on a specific protein. In the yeast two-hybrid system (Fields, S., et al., Trends Genet. 10 (1994) 286–292), the expression system of a gene library is designed so that when a given protein A acts on another protein B, transcription of the reporter gene employed is activated. In this method, the two functional domains of a DNA binding domain (DB) and a transcription activation domain (TA) are employed to activate transcription, and those proteins activating transcription in the gene expressing fused proteins having both of the domains (for example, when a fused protein of DB and protein A associates with a fused protein of TA and protein B) are screened. Recently, a method of analyzing the interaction between proteins based on surface plasmon resonance employing a laser beam has been developed.

Further, the screening of compounds affecting interaction between proteins, for example, compounds blocking or promoting interaction between proteins, has been conducted with protein pairs for which the interaction between proteins has been clearly specified. In that case, compounds affecting the above-mentioned protein pairs are screened from libraries of compounds comprising a large number of compounds.

The number of genes of human, mouse, and like is to be as high as 60,000 to 100,000. However, the number of genes known to date is still about 10,000, which is low relative to the whole. In recent years, the human genome project has been advancing and the number of genes that are being newly isolated and sequenced is increasing each year. This number is expected to continue to increase in the future. However, the functions of the genes that are being isolated and sequenced are often unknown. Since it is anticipated that all genes will eventually be specified, there is eagerly expected an appearance of the method that can systematically and rapidly analyze the functions of individual genes whose sequences are determined among the huge number of entire genes.

The present inventors conceived of the idea that it is possible to some extent to analyze the functions of genes by examining whether or not proteins having amino acid sequences coded by each gene interact with existing and new proteins.

As set forth above, known methods of analyzing interactions between proteins include immunoprecipitation, the phage display method, the yeast two-hybrid system, and surface plasmon resonance. However, immunoprecipitation requires antibodies against individual gene products (proteins). The preparation of antibodies corresponding to the entirety of genes lacks feasibility and there are problems on antibody specificity. In the phage display method and the yeast two-hybrid system, there is a frame restriction on the expression of prescribed genes as fused proteins, and even when the frames match, this does not mean that a specific gene is translated as a complete protein. There are limits to the size of the DNA that can be inserted in phage packaging. And in the yeast two-hybrid system, a DNA transformation into yeast is required and there is considerable inconvenience with regard to the systematic analysis of large numbers of samples. The surface plasmon resonance method requires the purification of each protein and is thus not currently suited to mass production analysis.

Thus, the detection of interaction between large quantities of proteins including new proteins and the selection of proteins that interact is impossible using existing methods.

Further, as set forth above, although there is a known method of screening for compounds affecting protein pairs whose protein—protein interaction has been clearly specified from compound libraries comprising large numbers of compounds, there is no known method of screening pairs of proteins affected by a given compound and the like among pairs of proteins formed as a result of interactions which are thought to be in a large number. Accordingly, it is an object of the present invention to provide a method of readily and rapidly detecting interactions between large numbers of proteins including new proteins.

A further object of the present invention is to provide a method that is capable of simply, efficiently, and systematically detecting which gene products (proteins) interact with each other even when the entire genes have been isolated, that is useful for inferring the functions of proteins.

A still further object of the present invention is to provide a method of screening pairs of proteins that are affected by a given compound from among multiple pairs of proteins.

DISCLOSURE OF THE INVENTION

The present invention relates to a method for the detection of interacting proteins, characterized by: mixing a protein having a label for detection synthesized by a cell-free protein synthesis method with a protein having a modification for separation synthesized by a cell-free protein synthesis method; separating, by means of the modification for separation, a protein pair formed by the interaction between the proteins from proteins having labels for detection that have not formed protein pairs; and identifying the protein pair by means of the label for detection (referred to hereinafter as Detection Method 1).

Further, the present invention relates to a method for the detection of interacting proteins, characterized by: synthesizing proteins having a label for detection and proteins having a modification for separation in a single system by a cell-free protein synthesis method; separating a protein pair formed by the interaction between proteins from proteins having a label for detection that have not formed protein pairs by using of the modification for separation; and identifying the protein pairs by using the label for detection (referred to hereinafter as Detection Method 2).

Still further, the present invention relates to a method for the detection of interacting proteins, characterized by: preparing a substrate dotted with proteins synthesized by a cell-free protein synthesis method, contacting a protein having a label for detection and which were synthesized in a cell-free protein synthesis method with the substrate dotted with proteins, and identifying protein pairs formed between the dotted proteins and labeled proteins by using the label for detection (referred to hereinafter as Detection Method 3).

Still further, the present invention relates to a method for screening protein pairs in which at least one substance affects the interaction between the proteins of a protein pair comprising the steps of:

(1-1) mixing, in presence of at least one substance affecting the interaction between the proteins of a pair, a protein having a label for detection synthesized by a cell-free protein synthesis method and a protein having a modification for separation synthesized by a cell-free protein synthesis method; separating protein pairs, formed by the interaction between proteins, from proteins having a label for detection that have not formed protein pairs by using the modification for separation, and identifying the protein pairs by use of the label for detection;

(1-2) performing the same process as in step (1-1) except that the mixing of the protein is conducted in absence of the substance; and (1-3) comparing the protein pairs identified in step (1-1) and in step (1-2) to determine protein pairs in which the interaction between proteins is affected by this substance (referred to hereinafter as Screening Method 1).

Still further, the present invention relates to a method for screening protein pairs in which at least one substance affects the interaction between the proteins of a protein pair comprising the steps of:

(2-1) synthesizing proteins having a label for detection and proteins having a modification for separation in a single system by a cell-free protein synthesis method; adding to the synthesis system at least one substance, affecting the interaction between the proteins of a pair; separating protein pairs formed by the interaction between proteins from proteins having a label for detection that have not formed a pair by using the modification for separation; and identifying the protein pairs by use of the label for detection;

(2-2) performing the same process as in step (2-1) with the exception that the mixing of the protein is conducted in absence of the substance; and (2-3) comparing the protein pairs identified in step (2-1) and in step (2-2) to determine protein pairs in which the interaction between proteins is affected by this substance (referred to hereinafter as Screening Method 2).

Still further, the present invention relates to a method for screening protein pairs in which at least one substance affects the interaction between the proteins of a protein pair comprising the steps of:

(3-1) preparing a substrate dotted with proteins synthesized by a cell-free protein synthesis method; contacting a protein having a label for detection, synthesized by a cell-free protein synthesis method, with the substrate dotted with proteins in presence of at least one substance, affecting the interaction between the proteins of a pair; and identifying protein pairs formed between the dotted proteins and the labeled proteins by use of the label for detection;

(3-2) performing the same process as in step (3-1) with the exception that the mixing of the protein is conducted in absence of the substance; and (3-3) comparing the protein pairs identified in step (3-1) and in step (3-2) to find a protein pair in which the interaction between proteins is affected by the above substance (referred to hereinafter as Screening Method 3).

MODES FOR CARRYING OUT THE INVENTION

There were five points that had to be taken care for accomplishing the present invention. First, how to prepare a large number of proteins. Second, how to label a prescribed protein for detection. Third, how to modify a prescribed protein for isolation. Fourth, whether it is possible to develop a system for simultaneously processing large numbers of samples. And fifth, whether it is possible to screen interactions between proteins affected by specified compounds.

The present invention is described in detail below, including these five points.

In Detection Methods 1–3 of the present invention, a protein having a label for detection and a protein having modification for separation are synthesized by a cell-free protein synthesis method.

Cell-free protein synthesis methods are well known. Kits for cell-free protein synthesis are commercially available. An example of a commercial kit suitable for use is the In Vitro Translation system made by Promega. Such kits can be employed in the present invention.

The starting material for the synthesis of a protein by a cell-free protein synthesis method may be either DNA or RNA. However, in employing DNA as the starting material, RNA, the transcriptional product of DNA, serves as the template in protein synthesis.

For example, using a cell-free system, cDNA can be transcribed into mRNA and the mRNA translated into a protein. A promoter for RNA polymerase is added to cDNA and the mRNA produced is translated into a protein in a cell-free protein synthesis system. RNA polymerases of phages such as T7, T3 and SP6 are conveniently employed as RNA polymerases; however, the present invention is not limited thereto. Rabbit reticulocyte lysate and wheat germ lysate are often employed as cell-free protein synthesis systems, but these are not by way of limitation. Although it is convenient to transcribe and translate simultaneously, they can also be done separately. For example, a kit for simultaneous transcription and translation is commercially available (a kit from Promega Co. is available under the name "TNT Lysate Coupled Transcription/Translation"). In a living organism, biosynthesized proteins are subjected to various modifications such as processing and glycosylation. When higher-level structures such as in modifications after the translation and receptors are required, microsomal fractions or/and membrane fractions can be added.

One or more kinds of proteins can be synthesized by cell-free protein synthesis. One kind of protein can be synthesized using a DNA or RNA as template and two or more kinds of proteins can be synthesized using two or more DNA or RNA as templates.

The use of a full-length strand cDNA library comprising multiple full-length strands of cDNA as genes and the synthesis of proteins by cell-free protein synthesis using this library as templates permits the preparation of samples comprising a variety of proteins. The present inventors have already employed basic techniques of efficiently preparing a full-length strand cDNA library (Carninci et al., Genomics 37 (1996) 327–336; Carninci et al.: DNA Res. 4 (1997) 61–66) and developed a device (RISA) capable of simultaneously analyzing the base sequence of multiple DNA clones (The Development of a 384 Multicapillary Sequencing System: Notes From the $21^{st}$ Annual Japan Molecular Biology Conference, 1P-570 (December, 1998, Yokohama)). As a result, the present inventors have prepared a number of full-length strand cDNA libraries from a variety of tissues and successfully established cataloged large-scale libraries with little redundancy (released to the public on the Riken home page. The number therein has now reached about 20,000 and is being updated daily.

In particular, the incorporation of labels for detection and modifications for separation can be accomplished by employing during the course of protein synthesis amino acid mixture containing amino acids which have a label for detection and/or a modification for separation (however, there are cases when amino acids described below and corresponding to amino acids having a label for detection and/or modification for separation are omitted) to synthesize a protein having a label for detection and/or a modification for separation. Alternatively, instead of amino acids having a label for detection and/or a modification for separation, an aminoacyl tRNA derivative having a label for detection and/or a modification for separation may be employed to incorporate labels for detection and/or modification for separation to the protein. Examples of aminoacyl tRNA derivatives are lysyl tRNA derivatives. Further, instead of amino acids having a label for detection and/or a modification for separation, puromycin derivatives having labels for detection and/or modifications for separation may be employed to incorporate labels for detection and/or modification for separation to the protein.

The label for detection to be incorporated into the protein may be a fluorescent substance, chemiluminescent substance, radioisotope, or stable isotope.

The labeling for detection of the prescribed protein can be done by addition of label-use amino acids to the cell-free transcription and translation system described above. Any amino acids for labeling for detection such as radioactive labels such as [35S] methionine, [35S] cysteine, [3H] leucine, and [14C] leucine, as well as chemiluminescent labels and fluorescent labels, and labels with stable isotopes may be employed, if a measurement method suited to the label is used. Amino acids with radioactive labels are commercially available. Further, labeled amino acid derivatives may be employed as aminoacyl tRNA amino acids. For example, NBD labeled lysyl tRNA is known as fluorescent lysyl tRNA (Crowley, K. S. et al., Cell 73 (1993) 1101–1115). It is also commercially available. In addition to fluorescent labels, chemiluminescent and stable isotopes may be employed as labels in the form of amino acid derivatives. Recently, it has been reported that when a puromycin derivative (Pur) was added to the cell-free protein synthesis system under specific conditions, the Pur was incorporated into the C terminus of the protein synthesized (Yanagawa, Hiroshi et al., "C-Terminal Fluorescent Labeling of Proteins", Notes From the $20^{th}$ (1997) Annual Japan Molecular Biology Conference, 3.501. P505; Miyamoto, Etsuko et al., "The Stop Codon Site Specific Linking of Puromycin and Its Analogs in Full-Length Proteins", Notes From the $20^{th}$ (1997) Annual Japan Molecular Biology Conference, 3.501. P508). Accordingly, when the C-terminus of the protein synthesized by the cell-free system is actually labeled based on that method, it is possible to obtain labeled full-length proteins in the synthesis using various mRNA as template.

Further, modification for solid-phase treatment is an example of modification for separation that can be incorporated into a protein having modification for separation. Biotinylation, avidinylation, and streptoavidinylation are further examples of modification for separation. Magnetic microbeads can also be employed as a modification for separation.

The modification for separation of a prescribed protein permits the ready recovery of the protein using the above-described cell-free transcription and translation system with solid phase treated with avidin or streptoavidin when the protein has been labeled with biotin or the like. It suffices to prepare tRNA carrying biotinylated amino acid as the protein biotinylation reagent. For example, in order to biotinylate lysine, biotinylated lysine-tRNA is commercially available for use. Further, biotinylated puromycin can be synthesized for use as the above-described puromycin derivative.

In Detection Method 1 of the present invention, a protein having a label for detection and a protein having a modification for separation are synthesized in separate systems and mixed.

In Detection Method 2 of the present invention, a protein having a label for detection and a protein having a modification for separation are synthesized in a single reaction system. The synthesis in a single reaction system of a protein having a label for detection and a protein having a modification for separation may be accomplished, for example, by mixing an amino acid having a label for detection and an amino acid having a modification for separation in a reaction system.

In Detection Method 1, interaction between proteins is conducted following mixing. In Detection Method 2, protein synthesis and the protein interaction occur in parallel. However, in this case, for example, a puromycin derivative or the like is employed and the label for detection and modification for separation are prevented from being introduced into the same protein. Examples of the conditions for forming a pair of proteins through the interaction of proteins are as follows.

First, a protein with modification for separation (for example, a biotinylated protein) and a protein labeled for detection (for example, a 35Met-labeled protein) are mixed together and caused to interact. The mixing ratio of the two proteins can be basically 1:1. When a kit is employed for the synthesis of proteins, for example, 2.5 µL of each (equivalent to a 7.5–15 ng quantity of protein) is admixed. In this case, the quantities of solution and protein added are not specifically limited, but when mixing multiple proteins at once, the quantity of each protein is, for example, 0.75–1.5 ng at a minimum and there is no upper limit. However, the quantity of protein required for detection may be suitably selected based on the type of label used for detection and the detection method. The temperature and duration of protein mixing and subsequent interaction are not specifically limited. However, for example, they may be conducted at 0–42° C. for from 30 min to 24 hr, preferably for about one hour at about 4° C. Particularly when employing a protein synthesis reaction solution obtained using a kit without further processing, it is desirable to maintain a low temperature (for example, 4° C.) following mixing and to conduct interaction at such a temperature so that new protein is not synthesized. After interaction, the protein modified for separation is separated and recovered from the protein having a label for detection that has not formed protein pairs. For example, when biotinylated protein is employed, streptoavidin magnetic beads can be employed. The addition of the beads and the reaction of beads with proteins having modification for separation are preferably conducted while stirring the reaction solution. The separation temperature and duration are not specifically limited. For example, they may be conducted at 0–42° C. for from 5 min to 4 hr, preferably at a temperature of about 4° C. for about 30 min. Particularly when employing a protein synthesis reaction solution obtained using a kit without further processing, it is desirable to maintain a low temperature (for example, 4° C.) so that undesirable new protein is not synthesized, and to conduct separation while stirring.

Further, to avoid nonspecific adsorption, the addition of a nonspecific adsorption blocking substance such as skim milk is desirable. Under the above-stated conditions, the addition of about 2 mg of skim milk is sufficient. However, this quantity may be suitably varied based on conditions.

The beads are recovered with a magnet and washed well, after which the signal is detected.

The reaction conditions, recovery methods, and detection methods described herein may be suitably varied according to the type of modification for separation and label for detection. Further, in Detection Method 3, the interaction and separation conditions may be made identical to those set forth above.

The protein pairs formed through interaction have both a label for detection and modification for separation. First, utilizing the function of the modification for separation, the protein pairs are separated from the system (from the protein having modification for detection that has not formed protein pairs). For example, when the modification for separation is biotin, avidin, or streptoavidin, protein pairs are separated by using a solid phase on which a substance having affinity for such substances has been fixed and by fixing the protein pairs to the solid phase. In this process, proteins having modification for separation that have not formed protein pairs are simultaneously separated. The protein that has formed protein pairs can be distinguished from the protein that has not formed protein pairs by utilizing the function of the label for detection. That is, since the protein that has not formed protein pairs does not have labels for detection, it is not detected and only protein pairs having both a label for detection and a modification for separation are detected.

In the detection method of the present invention, when distinguishing between samples forming protein pairs (positive samples) and samples not forming protein pairs (negative samples), as illustrated in the examples described below, a statistical method comparing deviation may be employed.

In Detection Method 3, a substrate dotted with protein synthesized by a cell-free protein synthesis method is prepared. Specifically, a protein having a modification for separation such as biotin, avidin, or streptoavidin serving as a modification for solid-phase treatment is synthesized and applied in dotting to a substrate. A substrate dotted with the protein can be made by contacting the biotinylated, avidinylated, or streptoavidinylated protein with a substrate on which a substance having affinity with biotin, avidin, or streptoavidin has been fixed. More specifically, biotin-labeled protein can be dotted on a substrate that has been coated with streptoavidin. Streptoavidin-coated substrates are commercially available. Alternatively, a streptoavidin-coated substrate can be manufactured using a magnetic substrate and magnetic streptoavidin (BioMag streptoavidin, PerSeptive Biosystems).

By contacting protein having a label for detection with the substrate that has been dotted with protein, protein pairs are formed with the protein on the substrate by interaction, and the protein is detected by utilizing the function of the label for detection possessed by the protein pairs. That is, although the dotted protein is present on the substrate, only protein forming protein pairs and having a label for detection is detected.

In Detection Methods 1 and 2 of the present invention, more specifically, the proteins having a label for detection are a protein group A comprising one or more types of proteins and the proteins having a modification for separation are a protein group B comprising one or more types of proteins. A protein pair (protein a-protein b) formed by interaction between a protein a belonging to protein group A and a protein b belonging to protein group B is separated from proteins having a label for detection that has not formed protein pairs by utilizing the modification for separation of protein b, and the protein pairs (protein a-protein b) that are separated is detected by the label that is possessed by the protein a.

Protein group A comprising protein having a label for detection may comprise one or more types of proteins. Protein group B comprising protein having a modification for separation may also comprise one or more types of proteins. For example, when detecting whether or not a protein interacting with a specific protein is present in a group of proteins comprising multiple unknown proteins, a group of multiple proteins a1, a2, a3, a4, and a5 may be employed as protein group A and just a specific protein b1 may be employed as protein group B, interaction may be conducted with protein b1, and thereby a protein a3 forming the protein pair (protein a3-protein b1), for example, may be detected. Conversely, a single specific protein a1 may be employed as protein group A and a protein group comprising multiple proteins b1, b2, b3, b4, and b5 may be employed as protein group B, interaction may be conducted with protein a1, and thereby a protein b4 forming the protein pair (protein a1-protein b4), for example, may be detected.

In Detection Method 3 of the present invention, more specifically, the protein having a label for detection is a protein group A comprising one or more types of proteins and the protein that is dotted on the substrate is a protein group B comprising one or more types of proteins. A protein pair (protein a-protein b) is formed by the interaction of a protein b belonging to protein group B that has been dotted on the substrate and a protein a belonging to protein group A. The label possessed by protein a in the protein pair (protein a-protein b) on the substrate is detected to select the protein interacting with the protein contained in protein group B.

As same as in Detection Methods 1 and 2, protein group A comprising proteins having labels for detection may comprise one or more types of proteins. Further, protein group B comprising proteins dotted on the substrate may comprise one or more types of proteins.

In the detection methods of the present invention, multiple syntheses by cell-free protein synthesizing methods and multiple interactions of proteins having a label for detection and/or proteins having a modification for separation may be done in parallel.

An example of a system capable of simultaneously processing multiple samples is a system in which protein synthesis reactions, protein interactions, and separation of protein pairs formed by interaction are conducted with multiwell plates having 96 or 384 wells. For example, in Detection Method 1 of the present invention, two multiwell plates are used to synthesize proteins having labels for detection and proteins having modifications for separation, the samples obtained in each well are mixed together, and the modification for separation possessed by the proteins is used to separate and detect proteins that interact.

In Detection Method 3 of the present invention, avidin or streptoavidin can be rendered as a solid phase on a flat plate in the same manner as in a DNA chip and the microchip of biotinylated protein is prepared and used. Both of these are suited to the use of robots and automation, permitting rapid processing of multiple samples.

The methods of the present invention envision, in the extreme, the synthesis of proteins corresponding to the entire genes of about 100,000 genes in a cell-free system and the detection of interaction between the proteins. Accordingly, in such a case, multiple synthesis by cell-free protein synthesis methods of proteins having labels for detection and/or proteins having modifications for separation and multiple interactions thereof are desirably conducted in parallel. Protein synthesis may be conducted for each gene or for two or more genes at a time. However, the proteins to be synthesized must include both proteins that are modified for separation and proteins that are labeled for detection.

Carrying out multiple processes in parallel means, for example, preparing micromultiwell plates with a total of 100,000 wells in horizontal line by 100,000 wells in vertical line, which give a total of 100,000×100,000 wells, with 100,000 types of proteins modified for separation being added to horizontal rows of wells and 100,000 types of proteins labeled for detection being added to vertical rows of wells, and determining which of the recovered proteins for separation exhibit label signals. By providing such a system, it becomes possible to detect interactions rapidly and conveniently even for multiple samples. Protein microtips in which 100,000 types of proteins for separation have been fixed in advance to substrates can be used as wells. The term "100,000 types of proteins" referred to here is by way of example, and the term "multiple" is not intended to be limited to "100,000 types of proteins".

Actually, two or more proteins can be added to a single well together. It is estimated that there are about 500,000 types of interactions between proteins and it is anticipated that interactions will be detected in a proportion of one per 20,000 combinations. A test employing about 20,000 combinations using microwell plates having 96 wells can be carried out as follows. One microwell plate having 96 wells is used to prepare 96 proteins having modifications for separation and one such plate is used to prepare proteins having labels for detection. The proteins on 32 wells in each plate are collected into one group (divided into three groups X, Y, and Z for separation and three groups x, y, and z for detection), and then interacted as the nine groups of Xx, Xy, Xz, Yx, Yy, Yz, Zx, Zy, and Zz. Each group comprises a combination of reactions of 32×32=1024. Nine groups comprise total 1024×9=9216, or about 10,000 combinations of proteins. By preparing two 96-well microwell plates each for separation and detection and providing combinations for interaction between 18 groups, it is theoretically possible to detect a pair of interacting proteins. Such a work may be done sufficiently by one person. Further automation or the use of robots permits the parallel testing of even greater numbers of samples. Further, adopting such the number of combinations as a yardstick, depending on conditions (number of samples or the like), it is suitably determined how many kinds of proteins should be mixed per well.

When modification for separation and labeling for detection are conducted with a puromycin derivative, it is possible to simultaneously conduct modification for separation and labeling for detection with a single tube (synthesis system). Thus, the operation becomes much simpler.

In the detection methods of the present invention, the following are examples of methods of searching for proteins forming protein pairs by interaction.

In Detection Method 1 of the present invention, a group of proteins comprising multiple proteins is employed as at least one of proteins having a label for detection and proteins having a modification for separation. For example, when a protein pair formed by interaction between proteins has been detected, the group of proteins comprising multiple proteins is divided into at least two subgroups. However, when both the proteins having a label for detection and the proteins having a modification for separation comprise multiple proteins, either protein group or both protein groups are divided into at least two subgroups. The subgroups are subjected again to the separation and detection of protein pairs formed by the interaction of proteins and the proteins forming protein pairs are determined. For example, ten groups each comprising ten proteins are prepared as protein groups comprising proteins having labels for detection and ten groups each comprising ten proteins are also prepared as protein groups comprising proteins having modifications for separation. The detection method of the present invention is applied to these 10×10 protein groups. For example, when a protein pair formed by the interaction between proteins in a combination of proteins having a label for detection and a protein having a modification for separation is detected, for example, each of the two protein groups is divided into five subgroups. Each subgroup (each subgroup comprising two proteins) (in this case, there are 5×5 combinations) is then subjected again to the detection method of the present invention and the protein pair formed by interaction between proteins is determined. The subgroup that has been determined is again subdivided (this time, there being 2×2 combinations comprising a single protein), and the detection method of the present invention is applied, finally revealing the protein pair formed by interaction between proteins. That is, until the subgroups comprise only a single protein, division into subgroups and separation and detection of protein pairs are repeated, permitting the determination of the desired protein pair formed by interaction between proteins.

In Determination Method 2 of the present invention, when at least one of the proteins having a label for detection and the protein having a modification for separation comprises multiple proteins and a protein pair formed by interaction between proteins is detected, the protein group comprising multiple proteins is divided into at least two subgroups. However, when both the protein having a label for detection and the protein having a modification for separation comprise multiple proteins, either protein group or both protein groups are divided into subgroups. The subgroups are then subjected again to the separation and detection of protein groups formed by interaction of proteins and the proteins forming the protein group are determined. The division into subgroups and the separation and detection of protein pairs can be repeated until the subgroup comprises only a single protein.

In Detection Method 3 of the present invention, when at least one of the proteins having a label for detection or the dotted protein comprises multiple proteins and a protein pair formed by interaction between proteins is detected, the protein group comprising multiple proteins is divided into at least two subgroups. However, when both the protein having a label for detection and the dotted protein comprise multiple proteins, either protein group or both protein groups are divided. The subgroups are further subjected to the separation and detection of the protein pair formed by the interaction of proteins and the proteins forming the protein pair are determined. The division into subgroups and the separation and detection of protein pairs is repeated until the subgroup comprises only a single protein.

In the above-described detection methods and the methods of screening of the present invention described further below; (1) the combinations of proteins having labels for detection and the proteins having modifications for separation may be combinations in which both the proteins having labels for detection and the proteins having modifications for separation are new proteins; (2) combinations in which the protein having a label for detection is a new protein and the protein having a modification for separation is a known protein; (3) combinations in which the protein having a label for detection is a known protein and the protein having a modification for separation is a new protein; and (4) combinations in which both the proteins having labels for detection and the proteins having modifications for separation are known proteins. In combination (1), it is possible to discover interacting protein pairs among unknown proteins. In combinations (2) and (3), it is possible to discover unknown proteins interacting with known proteins. And in combination (4), for example, it is possible to determine whether or not a protein known to cause an interaction with a protein having a modification for separation is present among proteins having a label for detection.

Accordingly, the detection methods of the present invention will permit the simple, efficient, and systematic detection of interactions between genetic products (proteins) when all genes have been isolated, are useful for inferring the functions of proteins, and can be applied to diagnostic systems.

Screening Method 1 of the present invention comprises the steps of (1-1) through (1-3) below.

Step (1-1): mixing of a protein having a label for detection synthesized by a cell-free protein synthesis method and a protein having modification for separation synthesized by a cell-free protein synthesis method in the presence of at least one substance; separating a protein pair formed by the interaction between proteins by means of the modification for separation; and identifying the protein pair by utilizing the label for detection. The synthesis by a cell-free protein synthesis method of the protein having a label for detection and the protein having a modification for separation, the separation by utilizing the modification for separation of the protein pair formed by interaction between proteins, and the identification of the protein pair by the label for detection can all be conducted by the same methods as in the above-described detection methods.

Further, the substance present during the mixing of the proteins is not specifically limited. Examples are: amino acids, peptides, proteins, lipids, sugars, and their derivatives. Further examples are: complexes of amino acids, peptides, proteins, lipids, sugars, and their derivatives. Additionally, the substance present during the mixing of proteins may be, for example, a natural organic substance or a derivative thereof such as an alkaloid, terpene, coenzyme, antibiotic, epolactaene or derivative thereof, benzophenone derivative, tetraazaeicosane, stachybocin, coumarin derivative, dipyridinium derivative, hirsutin derivative, cyclopropane derivative, allosamidin derivative, quinoline derivative, or quinocarcin or derivative thereof.

Further, the substance present during the mixing of the proteins may be a Chinese herbal drug or folk remedy. The symptoms for which Chinese herbal drugs and folk remedies are effective are known by experience, but it is well known that their actions are not well understood. For example, licorice is said to cure dropsy, rhubarb are said to cure severe diarrhea, and ephedra herb is said to cure insomnia. Accordingly, it is anticipated that what relations such substances have on which interactions between proteins can be screened by the methods of the present invention. It is also possible to specify which components comprising Chinese herbal drugs and popular remedies and what combinations thereof are effective. Examples of Chinese herbal drugs and popular remedies are given below.

Examples of Chinese herbal drugs are: Asini Corii Collas, gambir, sweet *hydrangea* leaf, benzoin, *clematis* root, *Artemisia capillaris* spica, fennel, tumeric, aconite root, *Prunus mume, lindera* root, bearberry leaf, rose fruit, *corydalis* tuber, *Isodon japonicus*, astragalus root, *scutellaria* root, *phellodendron* bark, pwedered *phellodendron* bark, cherry bark, *coptis* root, *polygala* root, *sophora* flower, *prunella* spike, *Terminalia chebula*, *Houttuynia* root, *Pogostemon cablin*, *pueraria* root, tale, Japanese *valerian*, Muller Argoviensis, *trichosanthes* root, Trichosanthis Semen, dried ginger, licorice, licorice powder, *cantharis*, agar pweder, Artemisiae Folium leaf, zedoary, *platycodon* root, powdered *platycodon* root, *chrysanthemum* flower, *catalpa* fruit, immature orange, *citrus* peel, *cinchona, notopterygium* root, apricot kernel, *Goodyera procera* flower, *Lycium chinense* seed, *Lycium chinense* leaf, *sophora* root, guaiac gum, *schizonepeta* herb, cinnamon bark, *cassia* seed, *pharbitis* seed, *Scrophularia ningpoensis, gentiana, geranium* herb, safflower, red *ginseng, cyperus* rhizome, Oryzae Semen, straw, *magnolia* bark, calumba, condurango, *achyranthes* root, *evodia* fruit, *arctium* fruit, *schisandra* fruit, *bupleurum* root, *asiasarum* root, saffron, *smilax* rhizome, hawthorn fruit, *gardenia* fruit, *cornus* fruit, *zanthoxylum* fruit, *Sophora subprostrata*, Zizyphi Spinosi Semen, *dioscorea* rhizome, pomegranate rind, *Aster tataricus*, *lithospermum* root, *perilla* seed, Tribuli Fructus, persimmon calyx, peony root, powdered peony root, *Adenophora triphylla*, *plantago* seed, *plantago* herb, gallnut, Amomi Semen, Zingiberis Rhizoma, cardamon, wheat, *cimicifuga* rhizome, Magnoliae Flos, *rehmannia* root, *Lycium chinense* bark, *Torilis japonica*, *houttuynia* herb, *Acorus gramineus* seed, gypsum, senega, powdered senega, *cnidium* rhizome, *nuphar* rhizome, cicada slough, *senna* leaf, powdered *senna* leaf, *swertia* herb, powdered *swertia* herb, gelatin, Peucedani Radix, *actractylodes lancea* rhizome, mulberry bark, Sappan Lignum, *perilla* herb, jujube, *alisma* rhizome, rhubarb, powdered rhubarb, Arecae Semen, Bambusae caulis, *panax* rhizome, *anemarrhena* rhizome, clove, Uncariae Uncis Cum Ramulus, chuling, *citrus unshiu* peel, *Arisaema serratum* tuber, *Gastrodia* tuber, *Asparagus cochinchinensis*, *Casicum annuum*, *capsicum*, Japanese *angelica* root, *Angelica pubescens* rhizome, peach kernel, bitter orange peel, ipecac, tragacanth, Araliae Cardatae Rhizoma, Amydae, nandin nut, *picrasma* wood, nutmeg, *ginseng*, honey-suckle, honey, *mentha* herb, *glehnia* root, *pinellia* tuber, fritillary bulbus, *ophiopogon* tuber, *Trapa natans* nut, Lilii Bulbus, *angelica dahurica* root, *atractylodes* rhizome, loquat leaf, *areca*, hoelen, aconite root, baked aconite root, sinomenium stem, *imperata* rhizome, *ledebouriella* root, Quercus Cortex, moutan bark, oyster shell, *ephedra* herb, *Cannabis* Fructus, *Vitex ritundifolia*, *akebia* stem, *Chaenomeles* fruit, *saussurea* root, bitter cardamon, *Leonurus sibiricus*, myricae cortex, *coix* seed, powdered *coix* seed, Longan Arillus, Fossilia Ossis Mastodi, magnesium sulfate, Gentianae Scabrae Radix, Alpiniae Officinari Rhizoma, *forsythia* fruit, Nelumbis Semen, *scopolia* rhizome, Araliae Cordatae Radix, and *Osmorhiza aristata* rhizome.

Examples of folk remedies are: *Mallotus japonicus* bark, *Taxus cuspidate*, *Gynostemma pentaphyllum*, *Epimedium marcranthum*, locust, bearberry leaf, *Quercus stenophylla*, *corydalis* tuber, *Isodon japonicus*, *Polygonatum falcatum*, *phellodendron* bark, *coptis* root, licorice, *pueraria* root, *Ajuga nipponensis* spike, *Artemisia vulgaris* leaf, Polygoni Multiflori Radix, persimmon leaf, persimmon juice, *platycodon* root, *Catalpa ovata*, *chrysanthemum* flower, *Ajuga decumbens*, *Goodyera procera* flower, *Polygonum filiforme*, *Sophora angustifola*, *Lycium chinense* fruit, *Lycium chinense* leaf, *Sasa albo-marginata*, mulberry leaf, *cassia* seed, *geranium* herb, safflower, *schisandra* fruit, *arctium* fruit, *Acanthopanax* bark, pepper, *Polygonum cuspidatum* rhizome, saffron, *smilax* rhizome, *gardenia* fruit, *rehmannia* root, *lithospermum* root, *plantago* herb, *houttuynia* herb, persimmon calyx, *Lycium chinense* bark, *dichroa* root, *Ligustrum lucidum*, earthworm, Aloes Lignum, leech, field horsetail, *dendrobium*, *senna* leaf, *swertia* herb, pomegranate, *Agrimonia Eupatoria*, cicada slough, mulberry bark, rhubarb, star anise, red ochre, *Aralia elata* bark, clove, *Lophatherum* leaf, dayflower, *Arisaema serratum* tuber, *Gastrodia* tuber, rush pith, *Corchorus* seed, *Ricinus communis* seed, *Codonopsis tangshen* root, *Trichosanthes* fruit, ipecac bark, *eucommia* bark, nandin nut, *Zea Mays*, *ginseng*, *Lonicera japonica*, frankincense, red-berried elder tree, *Patrinia scabiosaefolia* root, chickweed, *coix* seed, *Cassia occidentalis*, *senna* tea, *Tetragonia expansa*, pomegranate fruit, *Trapa natans* nut, loquat leaf, cluster *amaryllis* root, *Pyrrosia* leaf, *Stemona* root, *wisteria* bump, tabanidae, dandelion root, *Digenea simplex*, *Chaenomeles* fruit, *Actinidia polygama*, scouring rushes, peach leaf, *Daphniphyllum macropodum*, *Artemisia vulgaris* leaf, *Eupatorium stoechadosmum*, longana aril, *Glechoma hederacea*, Nelumbis Semen, and wasp's nest.

Substances in addition to those listed above (both known and unknown at the time of the filing of this application) may also be employed. A mixed system of two or more such substances may also be employed to determine the synergistic effects of multiple compounds on interaction between proteins.

Step (1-2): mixing of a protein having a label for detection synthesized by a cell-free protein synthesis method and a protein having modification for separation synthesized by a cell-free protein synthesis method in the absence of the above-stated substance; separating a protein pair formed by the interaction between proteins by means of the modification for separation; and identifying the protein pair based on the label for detection. This step is conducted in the same manner as step (1-1) except that mixing of the proteins is conducted in the absence of the above-described substance.

Step (1-3): comparing the protein pairs identified in step (1-1) and step (1-2) to find protein pairs in which the interaction of proteins is affected by the substance. For example, when a protein pair detected in step (1-1) conducted in the presence of the test substance is not detected in step (1-2) conducted in the absence of the test substance, it is found that the test substance has promoted the interaction between the proteins of the protein pair. Further, when a protein pair that was not detected in step (1-1) conducted in the presence of the test substance, is detected in step (1-2) conducted in the absence of the test substance, the test substance has blocked the interaction between the proteins of the protein pair. Further, it is possible to measure the degree of promotion or blocking of the interaction between proteins by varying the quantity of test substance present during mixing of the proteins.

Above-described steps (1-1) through (1-3) permit screening to determine which interactions between proteins of which protein pairs are affected by the above-described substances.

Screening Method 2 of the present invention comprises steps (2-1) through (2-3) below.

Step (2-1): synthesizing within a single system by a cell-free protein synthesis method a protein having a label for detection and a protein having a modification for separation, adding at least one compound to the synthesis system following synthesis, separating by means of the modification for separation a protein pair formed by the interaction between proteins in the presence of the above substance, and conducting identification of the protein pair based on the label for detection. The synthesis by a cell-free protein synthesis method of a protein having a label for detection and a protein having a modification for separation, the separation of a protein pair formed by the interaction between proteins based on the modification for separation, and the identification of the protein pair based on the label for detection may all be conducted in the same manner as in the above-described detection methods. Further, the substance that is present during the mixing of the proteins may be one exemplified as the substance described for Screening Method 1 described above. Still further, two or more of such substances may be employed in combination to determine the synergistic effects of multiple substances on interactions between proteins.

Step (2-2): synthesizing within a single system by a cell-free protein synthesis method a protein having a label for detection and a protein having a modification for separation, separating by means of the modification for separation a protein pair formed by the interaction between proteins in the absence of the substance, and conducting identification of the protein pair based on the label for detection. This step is the same as step (2-1) with the exception that the above-described substance is not added following synthesis of the proteins.

Step (2-3): comparing the protein pairs identified in step (2-1) and step (2-2) to find a pair of proteins the interaction of which is affected by the substance.

As in Screening Method 1, the above-described steps (2-1) through (2-3) permit screening to determine interaction between proteins of which protein pairs are affected by the above-described substances.

Screening Method 3 of the present invention comprises steps (3-1) through (3-3) below.

Step (3-1): preparing a substrate dotted with proteins synthesized by a cell-free protein synthesis method, contacting a protein having a label for detection synthesized by a cell-free protein synthesis method with the substrate dotted with the protein in the presence of at least one substance, and identifying, by means of the label for detection, a protein pair formed with the dotted protein as the result of interaction between proteins. Further, the substance that is present during the mixing of the proteins may be one exemplified as the substance described for Screening Method 1 described above. Still further, two or more of such substances may be employed in combination to determine the synergistic effects of multiple substances on interactions between proteins.

Step (3-2): preparing a substrate dotted with proteins synthesized by a cell-free protein synthesis method, contacting a protein having a label for detection synthesized by a cell-free protein synthesis method with the substrate dotted with the protein in the absence of the above-described substance, and identifying, by means of the label for detection, a protein pair forming with the dotted protein as the result of interaction between proteins. This step is identical to step (3-1) with the exception that the protein having a label for detection is contacted with the substrate in the absence of the above-described substance.

Step (3-3): comparing the protein pairs identified in step (3-1) and step (3-2) to find a pair of proteins the interaction of which is affected by the substance.

As same as in Screening Method 1, the above-described steps (3-1) through (3-3) permit screening to determined which interactions between which protein pairs are affected by the above-described substances.

The known immunosuppressors cyclosporine A and FK506 block the functioning of calcineulin, a protein phosphatase. In this process, it is known that cyclosporine A and FK506 first form complexes with proteins such as cyclophylin and FKBP (an FK506 binding protein) before becoming able to bind calcineulin (Liu, J. et al., Cell 66 (1991) 807–815). Accordingly, the interactions between proteins such as cyclophylin and calcineulin, or FKBP and calcineulin, can be screened by preparing compounds corresponding to cyclosporine A and FK506 in advance, interacting proteins in the presence and in the absence of these compounds, and measuring the effect of cyclosporine A and the like. Conversely, it is also possible to conduct screening of protein pairs the interaction of which is affected by certain substances among unspecified protein pairs. For example, cyclosporine A and FK506 can be employed to screen for protein pairs interacting in the same manner as protein pairs such as cyclophylin and calcineulin, or FKBP and calcineulin.

EXAMPLES

The present invention will be described in detail through Examples below.

In Reference Examples 1 and 2, it is showed that cell-free protein synthesis methods were employed to synthesize proteins from specific genes, and to recover and detect them. Further, Example 1 shows that proteins known to interact (such as SV40 large T and p53, or fos and jun) can actually be detected by the present methods.

The following were prepared as plasmid DNA for preparing proteins:

1) For luciferase expression: obtained from Promega Co. (attached to commercially available kit: TNT Rabbit Reticulocyte Lysate System)

2) For SV40 large T expression: SV40 DNA was purchased from BRL/Lifetech Co. The large T gene comprised two exons. Exon 1 was amplified by PCR. The primers employed were as follows:

SV40F: 5'-CCGGAATTCATGGATAAAGTTTTAAACA-GAGAG; (SEQ ID NO: 1)

SV40F: 5'-CCGGAATTCATGGATAAAGTTTTAAACA-GAGAG; (SEQ ID NO: 1)

A fragment enclosed between the EcoRI site (5' side of start codon ATG) and the Van91I site was cut out. For exon 2, a fragment enclosed between the Van91I site and the BamHI site (3' side of stop codon TGA) was cut out. Since the 3' and 5' ends of exons 1 and 2 were Van91I sites, the two fragments above were inserted into a pBluescript and cloned to obtain a SV40 large T expression-use plasmid.

3) For p53 expression: Riken clone 18B10009002Mr was amplified by PCR and employed. The primer employed was FP53:T7Kozak:Reverse=1:50:50. Each sequence was as follows.

FP53: 5'-GCCAATTGCCGCCACCATGACTGCCATG-GAGGAGTCAC;

(SEQ ID NO: 2)

T7Kozak: 5'-GAGCGCGCGTAATACGACTCACTAT-AGGGCCAATTGCCGCCACCATG;

(SEQ ID NO: 3)

Reverse: P8.

4) For fos expression: Riken clone 16B00000M11Ba was amplified by PCR and employed. The primer employed was FJun:T7Kozak:Reverse=1:50:50. The FJun sequence was as follows: 5'-GCCAATTGCCGCCACCATGATGT-TCTCGGGTTTCAACG.

(SEQ ID NO: 4)

5) For jun expression: Riken clone 28B10417F14Mr, whose 5' UTR portion with about 1,000 bases was removed, was employed.

Reference Example 1

Protein Synthesis from Genes (35S-Met Labeling)

Conducted with a cell-free protein synthesis kit (Promega Co. kit). The experimental conditions were as follows:

| | |
|---|---|
| Reticulocyte lysate | 12.5 μL |
| TNT buffer | 1 μL |
| TNT T7 polymerase | 0.5 μL |
| Amino acid mixture (Minus Met) 1 mM | 0.5 μL |
| 35S-Met | 1.0 μL |
| RNasin (40 units/μL) | 0.5 μL |
| DNA template* + H$_2$O | 9.0 μL |
| | (total 25 μL) |

*) Each DNA template was added as follows: for luciferase (1.0 ρg), for SV40 large T (1.0 μg), for p53 (0.5 μg), for fos (0.5 μg), for jun (1.0 μg).

After reacting for 1.5 hr at 30° C., the reaction was stopped by cooling with ice. 4 μL of TE4 and 5 μL of 2× sample buffer (total 10 μL) were added to 1 μL of the reaction solution and the mixture was heated for 3 min at 100° C. and subjected to SDS polyacrylamide electrophoresis (30 mA, about 1.5 hr of migration). After fixing, Coomassie dyeing, and drying, the RI band was detected with BAS2000.

Figure 1:
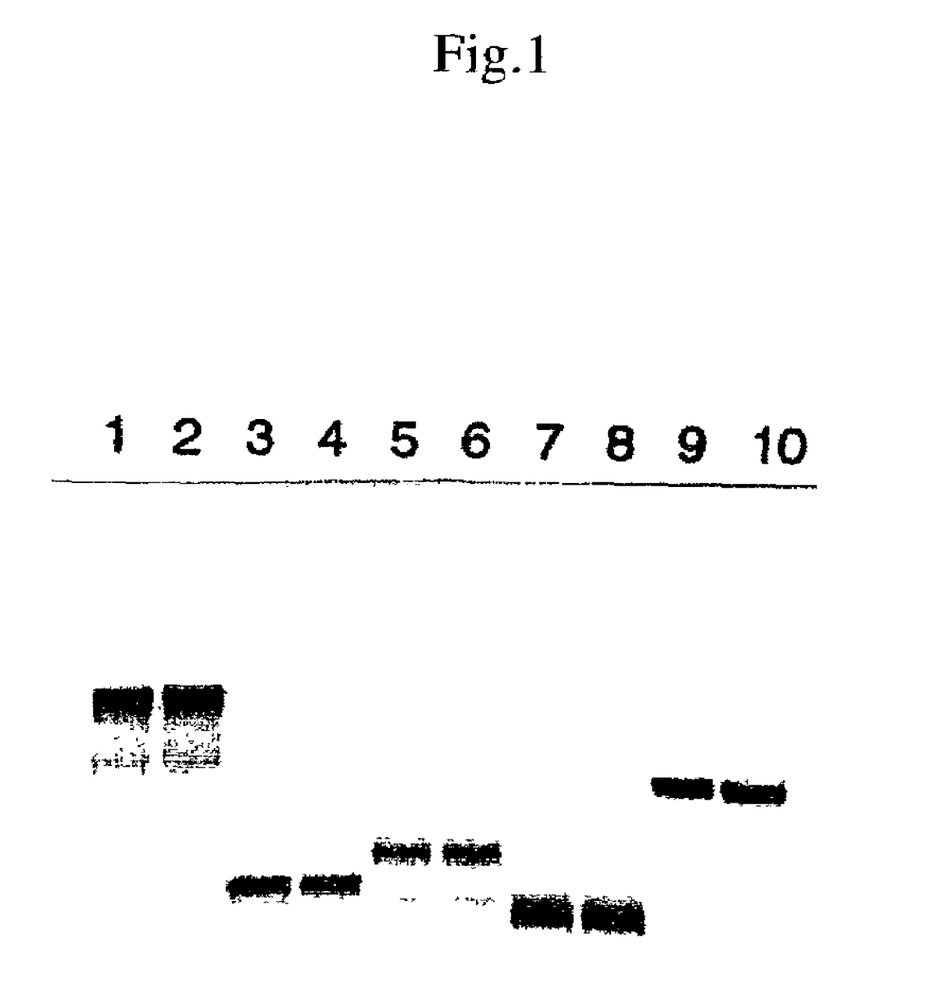
FIG. 1 shows the electrophoretic pattern of a 35S-labeled protein synthesized from individual cDNA plasmids with a cell-free protein synthesis system (transcription and translation system).

The results are shown in FIG. 1. In the figure, the DNA templates employed were as follows: lanes 1 and 2: for SV40 large T; lanes 3 and 4: for p53; lanes 5 and 6: for fos; lanes 7 and 8: for jun; lanes 9 and 10: for luciferase. Further, lanes 2, 4, 6, and 8 are the results of the supernatant recovered with the addition of streptoavidin beads following the reactions. These results show that a specific protein was synthesized for each DNA template and that the labeled proteins did not directly react with the streptoavidin beads.

Reference Example 2

Protein Synthesis from Genes (Biotin Labeling and Recovery of Biotinylated Protein)

Similar to the above-described $^{35}$S-Met labeling; 1 μL of 1 mM amino acid mixture was added in place of the 1 mM amino acid mixture (Minus Met) and 1 μL of biotinylated lysine tRNA (Transcent™ tRNA) was added in place of 35S-MET. When SDS polyacrylamide electrophoresis was conducted, a PVDF membrane was blotted and biotinylated protein was detected with a biotin detection kit (Behringer Co.)

Figure 2:
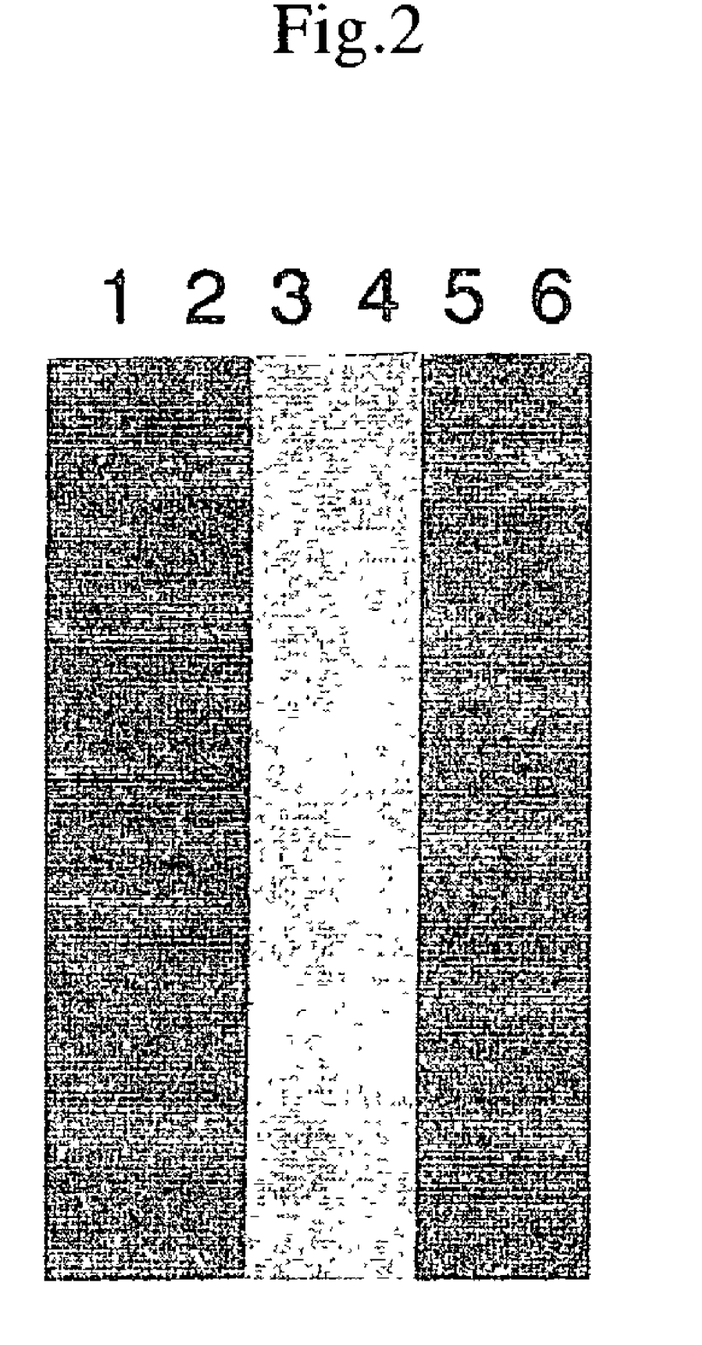
FIG. 2 shows the electrophoretic pattern of a biotinylated modification protein synthesized from individual cDNA plasmids with a cell-free protein synthesis system (transcription and translation system).

The results are shown in FIG. 2. The plasmids employed in the figure were as follows: lanes 1 and 2: for SV40 large T; lanes 3 and 4: for p53; and lanes 5 and 6: for luciferase. Lanes 2, 4, and 6 are the results of the supernatant recovered with the addition of streptoavidin beads following the reactions. The results show that a specific protein was synthesized for each DNA template and that the biotin-labeled proteins were reacted with streptoavidin beads and recovered. Although not described here, DNA templates for fos and jun were employed and the biotinylated protein was similarly prepared.

Example 1

Detection of Protein—Protein Interaction (Model System)

Reaction solutions of the RI-labeled protein of Reference Example 1 and the biotinylated protein of Reference Example 2 were mixed together in various combinations once the reactions had ended. That is, 2.5 μL of each reaction solution was mixed and placed on ice for 60 min. A 15 μL quantity of streptoavidin (Dynabeads) diluted with TBST-1 percent skim milk was added, and the mixture was stirred for 30 min at 4° C. Magnetic force was employed to recover the beads, thorough washing was conducted with TBST, and then the RI of the beads was measured. The results are given in Table 1. These results show that for SV40 large T and p53, and fos and jun, the interaction of which is well known, the isolation of one protein permitted the detection of the other. The interaction between SV40 large T was also detected.

TABLE 1

| Biotinylated | RI-Labeled Protein (c.p.m.) | | | | |
|---|---|---|---|---|---|
| Protein | Fos | Jun | Luc | Large T | P53 |
| Fos | 177 | <u>675</u> | 172 | 156 | 169 |
| Jun | <u>707</u> | 204 | 131 | 176 | 187 |
| Luc(a) | 152 | 150 | 148 | 127 | 233 |
| Large T | 197 | 197 | 208 | <u>551</u> | <u>1400</u> |
| p53 | 232 | 206 | 154 | <u>884</u> | 200 |

(a)Denotes luciferase

Example 2

Assaying of Multiple Samples (Model System)

A 1 μL quantity of each of the reaction solutions of five RI-labeled proteins of Reference Example 1 and 1 μL of each of the reaction solutions of five biotinylated proteins of Reference Example 2 were mixed together and placed on ice for 60 min. The same operation as in Example 1 was conducted and the RI of the beads was measured. The results showed that in the reactions of the five RI-labeled proteins with the five biotinylated proteins, a value of 1035 cpm was obtained. By contrast, a reaction of five RI-labeled proteins alone, without the addition of the biotinylated proteins, yielded a value of 447 cpm. This suggested that even when plural labeled proteins were mixed with plural biotinylated proteins, the interaction between proteins could still be adequately detected.

Example 3

Screening Methods

Labeled proteins were prepared according to Reference Example 1 (except that in the present experiment, an ultrafiltration membrane (Amicon) was employed to remove the free 35S-Met following the reaction) and biotinylated proteins were prepared according to Reference Example 2 for each of 320 known proteins arbitrarily selected from the Riken mouse full-length strand cDNA library ZX series (each of 1-1 through 1-12, 2-1 through 2-12, 3-1 through 3-12, and 4-1 through 4-4 was comprised of eight genes A–H). 16 proteins were mixed together into one group (1 μL of each labeled protein and 2 μL of each biotinylated protein, totaling 48 μL) and the interaction between a total of 20 groups of labeled protein and a total of 20 groups of biotinylated protein were examined in the same manner as in Example 2. Table 2 gives the detected RI (cpm) values. Table 3 give the statistical values (number (n), mean (m), and standard deviation (σ)) for the respective data. Table 4 gives the difference between the standard deviation (σ) in n=20 and the standard deviation (σ) in n=19 for each set of data (cpm).

TABLE 2

| | | P | 1- | | | | | | 2- | | | | | |
| --- | --- | --- | --- | --- | --- | --- | --- | --- | --- | --- | --- | --- | --- | --- |
| | | | 1.2 | 3.4 | 5.6 | 7.8 | 9,10 | 11.12 | 1.2 | 3.4 | 5.6 | 7.8 | 9,10 | 11.12 |
| 1- | 1.2 | 1,311 | 255 | 202 | 222 | 180 | 148 | 165 | 183 | 188 | 148 | 160 | 185 | 156 |
| | 3.4 | 1,357 | 288 | 343 | 299 | 309 | 245 | 377 | 349 | 363 | 271 | 289 | 325 | 353 |
| | 5.6 | 1,316 | 267 | 204 | 279 | 172 | 161 | 177 | 140 | 184 | 176 | 166 | 168 | 148 |
| | 7.8 | 1,106 | 168 | 191 | 176 | 219 | 160 | 187 | 178 | 202 | 170 | 192 | 207 | 157 |
| | 9,10 | 1,356 | 138 | 131 | 116 | 176 | 312 | 117 | 131 | 120 | 118 | 108 | 158 | 123 |
| | 11.12 | 978 | 89 | 85 | 96 | 87 | 89 | 94 | 100 | 104 | 87 | 96 | 118 | 88 |
| 2- | 1.2 | 1,052 | 264 | 382 | 226 | 232 | 236 | 195 | 218 | 350 | 203 | 206 | 1258 | 207 |
| | 3.4 | 1,019 | 256 | 250 | 257 | 254 | 268 | 240 | 365 | 323 | 262 | 293 | 288 | 231 |
| | 5.6 | 1,143 | 299 | 337 | 314 | 293 | 248 | 285 | 306 | 308 | 290 | 281 | 305 | 265 |
| | 7.8 | 841 | 142 | 195 | 198 | 144 | 177 | 168 | 189 | 159 | 133 | 179 | 151 | 154 |
| | 9,10 | 1,422 | 179 | 164 | 164 | 175 | 197 | 158 | 728 | 212 | 157 | 151 | 774 | 179 |
| | 11.12 | 759 | 141 | 155 | 160 | 175 | 150 | 153 | 151 | 151 | 147 | 145 | 168 | 127 |
| 3- | 1.2 | 1,103 | 231 | 255 | 244 | 207 | 214 | 243 | 224 | 252 | 230 | 264 | 243 | 207 |
| | 3.4 | 818 | 253 | 277 | 238 | 238 | 233 | 255 | 234 | 244 | 214 | 241 | 270 | 231 |
| | 5.6 | 750 | 140 | 164 | 268 | 138 | 146 | 157 | 150 | 147 | 141 | 186 | 174 | 140 |
| | 7.8 | 755 | 206 | 182 | 198 | 191 | 218 | 181 | 173 | 207 | 217 | 411 | 201 | 176 |
| | 9,10 | 731 | 139 | 150 | 151 | 145 | 159 | 139 | 165 | 166 | 140 | 150 | 140 | 147 |
| | 11.12 | 895 | 283 | 321 | 303 | 324 | 287 | 313 | 285 | 326 | 280 | 344 | 314 | 288 |
| 4- | 1.2 | 1,019 | 542 | 576 | 645 | 827 | 497 | 597 | 499 | 546 | 544 | 501 | 514 | 497 |
| | 3.4 | 852 | 307 | 267 | 258 | 227 | 253 | 235 | 255 | 248 | 240 | 231 | 234 | 224 |

| | | P | 3- | | | | | | 4- | |
| --- | --- | --- | --- | --- | --- | --- | --- | --- | --- | --- |
| | | | 1.2 | 3.4 | 5.6 | 7.8 | 9,10 | 11.12 | 1.2 | 3.4 |
| 1- | 1.2 | 1,311 | 181 | 214 | 195 | 212 | 168 | 205 | 162 | 155 |
| | 3.4 | 1,357 | 322 | 294 | 250 | 252 | 399 | 258 | 560 | 234 |
| | 5.6 | 1,316 | 176 | 169 | 170 | 158 | 162 | 159 | 153 | 141 |
| | 7.8 | 1,106 | 185 | 148 | 229 | 185 | 173 | 199 | 157 | 210 |
| | 9,10 | 1,356 | 109 | 115 | 99 | 121 | 140 | 114 | 111 | 151 |
| | 11.12 | 978 | 105 | 92 | 90 | 96 | 101 | 98 | 84 | 104 |
| 2- | 1.2 | 1,052 | 272 | 206 | 212 | 202 | 228 | 207 | 190 | 243 |
| | 3.4 | 1,019 | 273 | 306 | 243 | 284 | 268 | 269 | 246 | 267 |
| | 5.6 | 1,143 | 270 | 297 | 248 | 283 | 305 | 268 | 242 | 269 |
| | 7.8 | 841 | 163 | 151 | 157 | 187 | 167 | 182 | 152 | 151 |
| | 9,10 | 1,422 | 162 | 184 | 171 | 153 | 174 | 158 | 209 | 152 |
| | 11.12 | 759 | 145 | 163 | 126 | 145 | 172 | 137 | 147 | 156 |
| 3- | 1.2 | 1,103 | 314 | 178 | 238 | 229 | 338 | 236 | 201 | 206 |
| | 3.4 | 818 | 238 | 236 | 242 | 239 | 260 | 236 | 227 | 256 |
| | 5.6 | 750 | 166 | 139 | 142 | 215 | 168 | 164 | 135 | 167 |
| | 7.8 | 755 | 207 | 203 | 185 | 192 | 207 | 194 | 170 | 201 |
| | 9,10 | 731 | 143 | 165 | 140 | 167 | 163 | 161 | 132 | 145 |
| | 11.12 | 895 | 226 | 306 | 303 | 300 | 336 | 329 | 288 | 293 |
| 4- | 1.2 | 1,019 | 606 | 468 | 469 | 507 | 499 | 504 | 506 | 486 |
| | 3.4 | 852 | 238 | 258 | 221 | 362 | 246 | 239 | 228 | 269 |

TABLE 3

| | | n | m | σ | m + σ |
| --- | --- | --- | --- | --- | --- |
| 1- | 1.2 | 20 | 184 | 27 | 212 |
| | 3.4 | 20 | 319 | 72 | 391 |
| | 5.6 | 20 | 177 | 35 | 212 |
| | 7.8 | 20 | 185 | 21 | 206 |
| | 9,10 | 20 | 135 | 44 | 180 |
| | 11.12 | 20 | 95 | 8 | 103 |
| 2- | 1.2 | 20 | 287 | 228 | 515 |
| | 3.4 | 20 | 272 | 31 | 303 |
| | 5.6 | 20 | 286 | 24 | 310 |
| | 7.8 | 20 | 165 | 18 | 183 |
| | 9,10 | 20 | 230 | 175 | 405 |
| | 11.12 | 20 | 151 | 13 | 163 |
| 3- | 1.2 | 20 | 238 | 36 | 274 |
| | 3.4 | 20 | 243 | 14 | 258 |
| | 5.6 | 20 | 162 | 31 | 193 |
| | 7.8 | 20 | 206 | 49 | 255 |
| | 9,10 | 20 | 150 | 11 | 161 |
| | 11.12 | 20 | 302 | 25 | 328 |
| 4- | 1.2 | 20 | 542 | 80 | 622 |
| | 3.4 | 20 | 252 | 32 | 284 |

TABLE 4

| | | P | 1- | | | | | | -2 | | | | | | 3- | | | | | | 4- | |
|---|---|---|---|---|---|---|---|---|---|---|---|---|---|---|---|---|---|---|---|---|---|---|
| | | | 1.2 | 3.4 | 5.6 | 7.8 | 9,10 | 11.12 | 1.2 | 3.4 | 5.6 | 7.8 | 9,10 | 11.12 | 1.2 | 3.4 | 5.6 | 7.8 | 9,10 | 11.12 | 1.2 | 3.4 |
| 1- | 1.2 | 1,311 | 5 | -0 | 1 | -1 | 1 | -0 | -1 | -1 | 1 | -0 | -1 | 0 | -1 | 0 | -1 | 0 | -0 | -0 | -0 | 0 |
| | 3.4 | 1,357 | -2 | -2 | -2 | -2 | 0 | -1 | -2 | -1 | -1 | -2 | -2 | -1 | -2 | -2 | -0 | -0 | 1 | -0 | 25 | 1 |
| | 5.6 | 1,316 | 6 | -0 | 8 | -1 | -1 | -1 | 0 | -1 | -1 | -1 | -1 | -0 | -1 | -1 | -1 | -1 | -1 | -1 | -0 | 0 |
| | 7.8 | 1,106 | -0 | -1 | -0 | 1 | 0 | -1 | -0 | -0 | -0 | -0 | 0 | 0 | -1 | 1 | 2 | -1 | -0 | -0 | 0 | 0 |
| | 9,10 | 1,356 | -1 | -1 | -1 | -0 | 26 | -1 | -1 | -1 | -1 | -1 | -1 | -1 | -1 | -1 | -0 | -1 | -1 | -1 | -1 | -1 |
| | 11.12 | 978 | -0 | 0 | -0 | 0 | -0 | -0 | -0 | 0 | 0 | -0 | 2 | -0 | 0 | -0 | -0 | -0 | -0 | -0 | 0 | 0 |
| 2- | 1.2 | 1,052 | -6 | -5 | -5 | -6 | -6 | -5 | -5 | -5 | -5 | -5 | 178 | -5 | -6 | -5 | -5 | -5 | -6 | -5 | -5 | -6 |
| | 3.4 | 1,019 | -1 | -0 | -1 | -1 | -1 | 0 | 8 | 2 | -1 | -0 | -1 | 1 | -1 | 0 | -0 | -1 | -1 | -1 | -0 | -1 |
| | 5.6 | 1,143 | -0 | 3 | 0 | -1 | 1 | -1 | -0 | -0 | -1 | -1 | -0 | -0 | -0 | -0 | 1 | -1 | -0 | -0 | 2 | -0 |
| | 7.8 | 841 | 0 | 1 | 1 | 0 | -0 | -0 | 0 | -0 | 1 | -0 | -0 | -0 | -0 | -0 | 0 | -0 | -0 | -0 | -0 | -0 |
| | 9,10 | 1,422 | -4 | -4 | -4 | -4 | -4 | -4 | 39 | -4 | -4 | -4 | 49 | -4 | -4 | -4 | -4 | -4 | -4 | -4 | -4 | -4 |
| | 11.12 | 759 | -0 | -0 | -0 | 1 | -0 | -0 | -0 | -0 | -0 | -0 | 0 | 1 | -0 | -0 | 1 | -0 | 1 | 0 | -0 | -0 |
| 3- | 1.2 | 1,103 | -1 | -1 | -1 | -0 | -1 | -1 | -1 | -1 | -1 | -0 | -1 | -0 | 4 | 2 | -1 | -1 | 8 | -1 | 0 | -0 |
| | 3.4 | 818 | -0 | 2 | -0 | -0 | -0 | -0 | -0 | -0 | 1 | -0 | 1 | -0 | -0 | -0 | -0 | -0 | 0 | -0 | 0 | 0 |
| | 5.6 | 750 | -0 | -1 | 11 | -0 | -1 | -1 | -1 | -1 | -0 | -0 | -1 | -0 | -1 | -0 | -0 | 2 | -1 | -1 | -0 | -1 |
| | 7.8 | 755 | -1 | -1 | -1 | -1 | -1 | -1 | -1 | -1 | -1 | 35 | -1 | -1 | -1 | -1 | -1 | -1 | -0 | -1 | -1 | -0 |
| | 9,10 | 731 | 0 | -0 | -1 | -0 | -1 | 0 | 0 | 0 | -0 | -0 | -0 | -0 | -0 | 0 | -0 | 0 | 0 | 0 | 1 | -0 |
| | 11.12 | 895 | -0 | -0 | -1 | -0 | -0 | -1 | -0 | -0 | -0 | 1 | -1 | -0 | 7 | -1 | -1 | -1 | 1 | 0 | -0 | -1 |
| 4- | 1.2 | 1,109 | -2 | -2 | 2 | 33 | -1 | -1 | -1 | -2 | -2 | -2 | -2 | -1 | -1 | -0 | -0 | -2 | -1 | -2 | -2 | -1 |
| | 3.4 | 852 | 2 | -1 | -1 | -0 | -1 | -1 | -1 | -1 | -1 | -0 | -1 | -0 | -1 | -1 | -0 | 12 | -1 | -1 | -0 | -1 |

Table 2 shows the signal (cpm) detected when one group of the 20 groups (vertical axis) of labeled proteins was interacted with one group of the 20 groups (horizontal axis) of biotinylated proteins by the same method as in Example 2. The value as the positive control (P) is the value (see Example 1) obtained by adding 2 μL of biotinylated jun and 1 μL of 35S-Met labeled Fos, whose interaction is already known, to the same combination (corresponding to what is on the diagonal line in the table). For confirmation by means of statistical verification, the average value (m) and standard deviation (σ) were calculated for a number (n=20) of each of 35S-Met labeled protein groups (Table 3), and the subtracted value between this standard deviation and the standard deviation calculated similarly when n=19 is given in Table 4. This value indicates the degree of bias when each of the measured values in Table 2 was compared with the measured values of the other 19 groups. Theoretically, as this value is closer to 0, the bias is within an error range. At a reliability level of 95 percent, the bias is 21, and at a reliability level of 99 percent, the bias is 31. Here, combinations exhibiting values of 25 or greater were considered empirically significant and the experiment was continued.

For combinations of labeled proteins and biotinylated proteins exhibiting high signal values in the results of Table 2 as well as exhibiting values of 25 or greater in Table 4, and combinations exhibiting reproducibility in experiments on combinations where biotinylation and labeling were reversed (the combinations of 1-9, 10 and 1-9, 10 (Table 5), the combinations of 2-9, 10 and 2-1, 2 (Table 6), the combinations of 2-1, 2 and 2-9, 10 (Table 7), and 2-9, 10 and 2-9, 10 (Table 8)), the group of 16 proteins was further divided into four groups comprising four proteins and secondary interaction detection was conducted. The results are given in Tables 5–8.

TABLE 5

| | | | 1-9,10 | | | |
|---|---|---|---|---|---|---|
| | | P | AD | EH | AD | EH |
| 1-9,10 | AD | 423 | 40 | 28 | 50 | 29 |
| | EH | 374 | 125 | 212 | 44 | 51 |

TABLE 5-continued

| | | | 1-9,10 | | | |
|---|---|---|---|---|---|---|
| | | P | AD | EH | AD | EH |
| | AD | 421 | 37 | 55 | 44 | 56 |
| | EH | 445 | 38 | 33 | 37 | 38 |

TABLE 6

| | | | 2-9,10 | | | |
|---|---|---|---|---|---|---|
| | | P | AD | EH | AD | EH |
| 2-1,2 | AD | 413 | 43 | 49 | 54 | 45 |
| | EH | 414 | 84 | 44 | 40 | 357 |
| | AD | 389 | 38 | 39 | 34 | 38 |
| | EH | 391 | 41 | 34 | 43 | 48 |

TABLE 7

| | | | 2-1,2 | | | |
|---|---|---|---|---|---|---|
| | | P | AD | EH | AD | EH |
| 2-9,10 | AD | 454 | 71 | 43 | 55 | 67 |
| | EH | 380 | 56 | 48 | 42 | 37 |
| | AD | 379 | 56 | 60 | 54 | 46 |
| | EH | 698 | 101 | 481 | 123 | 73 |

TABLE 8

| | | | 2-9,10 | | | |
|---|---|---|---|---|---|---|
| | | P | AD | EH | AD | EH |
| 2-9,10 | AD | 413 | 111 | 52 | 65 | 52 |
| | EH | 414 | 42 | 48 | 58 | 53 |
| | AD | 389 | 57 | 53 | 57 | 49 |
| | EH | 391 | 105 | 101 | 76 | 533 |

In Tables 5–8 and Tables 9–11 described below, since the population number n was comparatively low 4 and was unsuited to statistical processing, combinations with high signal values were treated as candidates for subsequent detection. Generally, for the reliability level to exceed 95 percent, the population n must be 5, 6, or greater. Thus, when the population is 5, 6, or greater, combinations having significance can be evaluated by performing statistical processing.

For the combinations exhibiting high signal values in Tables 5–8 (combinations 2-1, E-H and 2-10, E-H (Table 9); combinations 2-10, E-H and 2-10, E-H (Table 10); and combinations 1-9, E-H and 1-9, E-H (Table 11)), each group comprising four proteins was divided into subgroups of single proteins and a third level of interaction detection was conducted. The results are given in Tables 9–11.

TABLE 9

|      |   | 2-1   |     |     |     |     |
|------|---|-------|-----|-----|-----|-----|
|      |   | P     | E   | F   | G   | H   |
| 2-10 | E | 1,824 | 141 | 58  | 59  | 189 |
|      | F | 1,584 | 60  | 60  | 72  | 736 |
|      | G | 1,592 | 117 | 308 | 114 | 97  |
|      | H | 1,742 | 91  | 101 | 57  | 68  |

TABLE 10

|      |   | 2-10  |      |     |     |     |
|------|---|-------|------|-----|-----|-----|
|      |   | P     | E    | F   | G   | H   |
| 2-10 | E | 1,824 | 1932 | 95  | 90  | 111 |
|      | F | 1,584 | 87   | 168 | 67  | 98  |
|      | G | 1,592 | 116  | 137 | 146 | 78  |
|      | H | 1,742 | 314  | 64  | 352 | 73  |

TABLE 11

|     |   | 1-9 |     |    |    |    |
|-----|---|-----|-----|----|----|----|
|     |   | P   | E   | F  | G  | H  |
| 1-9 | E | 367 | 225 | 32 | 36 | 37 |
|     | F | 240 | 37  | 33 | 38 | 35 |
|     | G | 261 | 35  | 40 | 43 | 38 |
|     | H | 235 | 47  | 41 | 40 | 36 |

Finally, from the 102, 400 (320×320) combinations, the following three protein interactions could be identified.

1) DnaJ-like protein (Hsj2) (2-10E)/DnaJ-like protein (Hsj2) (2-10E) (self-association)

2) Caspase 6 (1-9E)/Caspase 6 (1-9E) (self-association)

3) Bpx protein (nucleosome assembly protein homologue) (2-1H)/MB20 protein (function unknown, 2-10F)

Of these, 1) is a dimer of known interaction (Wickner: Proc. Natl. Acad Sci, USA 87 (1990) 2,690–2,694) and 2) and 3) are known proteins of unknown function. With respect to 3), a search of the literature revealed that the protein Bpx corresponds to a NAP 1-like protein L2 belonging to the NAP (nucleosome Assembly protein) 1 family (Rougeulle et al.: Hum. Mol. Genet. 5 (1996) 41–49). Further, a search for homology based on the BLAST1 of the amino acid sequence predicted from the base sequence revealed protein MB20 to be an NAP1-like protein L3 belonging to the same NAP1 family.

The present invention provides methods capable of readily and rapidly detecting interactions between large numbers of proteins including new proteins. These methods permits the simple, efficient, and systemic detection of interacting genetic products (proteins) even when all genes have been isolated, and they are useful for inferring protein functions. That is, interactions between proteins can be systematically detected by labeling for detection and modifying for isolation proteins obtained from each clone of catalogued full-length strand cDNA large-scale libraries.

Further, the screening methods of the present invention permit the detection of pairs of proteins that are affected by certain compounds, for example, organism-related substances and natural organic substances, from among plural protein pairs. The use of the screening methods of the present invention permits the clarification of how interactions between proteins are affected by organism-related substances and compounds that are known to be pharmacologically active but the action mechanisms of which are unknown.

The invention claimed is:

1. A method for determining interacting proteins, comprising:
   i) synthesizing in a cell-free synthesis method at least one first group of proteins wherein said first group comprises one or more proteins bearing a label for detection and at least one second group of proteins wherein said second group comprises one or more proteins bearing a modification that provides for solid-phase separation;
   ii) mixing said at least one first group of proteins bearing a label for detection with said at least one second group of proteins bearing a modification that provides for solid-phase separation;
   iii) separating, by binding to a solid phase, one or more protein pairs formed by the interaction between a protein of the first group of proteins and a protein of the second group of proteins from proteins having labels for detection that have not formed protein pairs;
   iv) detecting the protein pair by detecting the label for detection;
   v) identifying at least one first group of proteins and at least one second group of proteins that include at least one protein pair;
   vi) dividing the at least one first group of proteins including a protein pair into at least two sub-groups and dividing the at least one second group of proteins including a protein pair into at least two sub-groups; and
   vii) repeating steps i) to vi) for each sub-group until the proteins forming protein pairs are determined.

2. The method according to claim 1, wherein the division into subgroups and the separation and detection of the protein pairs are repeated until the subgroups no longer comprise a plurality of different protein pairs.

3. The method according to 1 in which the at least one first group of proteins comprises more than one different proteins, each bearing the same label for detection.

4. The method according to claim 1 in which the at least one second group of proteins comprises more than one different proteins, each bearing the same label for separation.

5. The method according to claim 1 in which the at least one first group of proteins comprises more than one different proteins bearing a plurality of different labels for detection.

6. The method according to claim 1 in which the at least one second group of proteins comprises more than one different proteins, bearing a plurality of different labels for separation.

7. The method according to claim 1, in which the detection label is a fluorescent substance, a chemiluminescent substance, a radioisotope or a stable isotope and is covalently attached to the at least one first protein.

8. The method according to claim 1, in which the modification for separation is biotinylation, avidinylation or streptavidinylation and the separation is performed by contacting the mixture of proteins with a solid phase upon which a substance having affinity for biotin, avidin or strepavidin, respectively, is fixed.

9. The method according to claim 1, in which the label for detection and/or modification for separation of the proteins is introduced into the proteins by using an aminoacyl tRNA derivative during synthesis of the proteins.

10. The method according to claim 9, in which the aminoacyl tRNA derivative is a lysyl tRNA derivative.

11. The method according to claim 1, in which the label for detection are introduced into the first proteins and the modification for separation of the second proteins are introduced into the proteins by using a puromycin derivative during synthesis of the proteins.

12. The method according to claim 11, in which a fluorescence-labeled or radioisotope-labeled puromycin is used as a puromycin derivative for introducing the label for detection and biotinylated puromycin is used as a puromycin derivative for introducing the modification for separation.

13. The method according to claim 1, in which the proteins of each group are synthesized together by a cell-free synthesis method and the mixing of the proteins in step ii) is performed coincident with the synthesis of the proteins.

14. The method according to claim 1, in which the template for the cell-free protein synthesis is either DNA or RNA.

* * * * *

SEQUENCE LISTING

<160> NUMBER OF SEQ ID NOS: 4

<210> SEQ ID NO 1
<211> LENGTH: 33
<212> TYPE: DNA
<213> ORGANISM: Artificial Sequence
<220> FEATURE:
<223> OTHER INFORMATION: PCR Primer

<400> SEQUENCE: 1
ccggaattca tggataaagt tttaaacaga gag         33

<210> SEQ ID NO 2
<211> LENGTH: 38
<212> TYPE: DNA
<213> ORGANISM: Artificial Sequence
<220> FEATURE:
<223> OTHER INFORMATION: PCR Primer

<400> SEQUENCE: 2
gccaattgcc gccaccatga ctgccatgga ggagtcac         38

```
<210> SEQ ID NO 3
<211> LENGTH: 47
<212> TYPE: DNA
<213> ORGANISM: Artificial Sequence
<220> FEATURE:
<223> OTHER INFORMATION: PCR Primer

<400> SEQUENCE: 3
gagcgcgcgt aatacgactc actatagggc caattgccgc caccatg          47

<210> SEQ ID NO 4
<211> LENGTH: 38
<212> TYPE: DNA
<213> ORGANISM: Artificial Sequence
<220> FEATURE:
<223> OTHER INFORMATION: PCR Primer

<400> SEQUENCE: 4
gccaattgcc gccaccatga tgttctcggg tttcaacg                    38
```